(12) United States Patent
Classen et al.

(10) Patent No.: US 9,345,808 B2
(45) Date of Patent: May 24, 2016

(54) STRUCTURE HAVING FIBRES WHICH ARE ADHESIVELY BONDED TO ONE ANOTHER IN LOCATIONS

(71) Applicant: Occlutech Holding AG, Schaffhausen (CN)

(72) Inventors: Christoph Classen, Monschau (DE); Swen Franzen, Köln (DE); Harrie Van Baars, Hengelo (NL); Wolfgang Witt, Moers (DE); Andreas Henseler, Simmerath (DE); Frank Willems, Moers (DE)

(73) Assignee: Occlutech Holding AG, Schaffhausen (CH)

( * ) Notice: Subject to any disclaimer, the term of this patent is extended or adjusted under 35 U.S.C. 154(b) by 0 days.

(21) Appl. No.: 14/369,667

(22) PCT Filed: Dec. 19, 2012

(86) PCT No.: PCT/DE2012/001211
§ 371 (c)(1),
(2) Date: Jun. 27, 2014

(87) PCT Pub. No.: WO2013/097841
PCT Pub. Date: Jul. 4, 2013

(65) Prior Publication Data
US 2014/0364937 A1    Dec. 11, 2014

(30) Foreign Application Priority Data

Dec. 29, 2011 (DE) .......................... 10 2011 122 490
May 3, 2012 (DE) .......................... 10 2012 008 656

(51) Int. Cl.
| | | |
|---|---|---|
| A61F 2/06 | (2013.01) | |
| A61L 27/18 | (2006.01) | |
| A61L 31/06 | (2006.01) | |
| A61L 31/10 | (2006.01) | |
| A61L 31/14 | (2006.01) | |
| A61L 31/16 | (2006.01) | |
| A61L 27/34 | (2006.01) | |
| A61L 27/50 | (2006.01) | |
| A61F 2/82 | (2013.01) | |
| A61L 27/58 | (2006.01) | |
| D04H 1/4358 | (2012.01) | |
| D04H 1/58 | (2012.01) | |
| D04H 1/64 | (2012.01) | |
| D04H 3/009 | (2012.01) | |
| D04H 3/02 | (2006.01) | |
| D04H 3/07 | (2012.01) | |

(52) U.S. Cl.
CPC . *A61L 27/18* (2013.01); *A61F 2/06* (2013.01); *A61F 2/82* (2013.01); *A61L 27/34* (2013.01); *A61L 27/50* (2013.01); *A61L 27/507* (2013.01); *A61L 27/58* (2013.01); *A61L 31/06* (2013.01); *A61L 31/10* (2013.01); *A61L 31/14* (2013.01); *A61L 31/148* (2013.01); *A61L 31/16* (2013.01); *A61L 2400/18* (2013.01); *D04H 1/4358* (2013.01); *D04H 1/58* (2013.01); *D04H 1/64* (2013.01); *D04H 3/009* (2013.01); *D04H 3/02* (2013.01); *D04H 3/07* (2013.01)

(58) Field of Classification Search
CPC ........... A61F 2/06; A61F 27/507; D04H 3/07; D04H 3/073; A61L 31/00; A61L 31/14
See application file for complete search history.

(56) References Cited

U.S. PATENT DOCUMENTS

| | | | | |
|---|---|---|---|---|
| 5,851,229 | A * | 12/1998 | Lentz et al. ................ | 623/23.72 |
| 2002/0040247 | A1 | 4/2002 | Castro et al. | |
| 2005/0079781 | A1 * | 4/2005 | Tsujimoto et al. .............. | 442/59 |
| 2006/0009835 | A1 * | 1/2006 | Osborne et al. ............. | 623/1.13 |
| 2010/0119578 | A1 * | 5/2010 | To et al. ........................ | 424/423 |

FOREIGN PATENT DOCUMENTS

| | | |
|---|---|---|
| DE | 102009037134 A1 | 2/2011 |
| EP | 0237037 A2 | 9/1987 |
| EP | 2042203 A2 | 4/2009 |
| WO | WO02/49536 A2 | 6/2002 |
| WO | WO2008/049396 A1 | 5/2008 |
| WO | WO2011/054932 A1 | 5/2011 |

OTHER PUBLICATIONS

WIPO, European International Search Authority, International Search Report mailed May 28, 2013 in International Patent Application No. PCT/DE2012/001211, 5 pages.

* cited by examiner

*Primary Examiner* — David Isabella
*Assistant Examiner* — Suba Ganesan
(74) *Attorney, Agent, or Firm* — Inskeep IP Group, Inc.

(57) ABSTRACT

The invention relates to a structure having fibers which are adhesively bonded to one another in locations and have a permeability for air of between 0.5 ml/min*$cm^2$ and 1.5 ml/min*$cm^2$, wherein said structure has an at least one-sided coating which reduces the permeability of the structure to below 0.2 ml/min*$cm^2$.

10 Claims, No Drawings

STRUCTURE HAVING FIBRES WHICH ARE ADHESIVELY BONDED TO ONE ANOTHER IN LOCATIONS

RELATED APPLICATIONS

This application is the U.S. National Phase of and claims priority to International Patent Application No. PCT/DE2012/001211, International Filing Date Dec. 19, 2012, entitled Structure Having Fibres Which Are Adhesively Bonded To One Another In Locations, which claims benefit of German Application No. DE102011122490.8, filed Dec. 29, 2011entitled Structur mit stellanweise miteinander verklebten Fasern; and German Application No. DE102012008656.3, filed May 3, 2012entitled Structur mit stellanweise miteinander verklebten Fasern; all of which are incorporated herein by reference in their entireties.

The invention relates to a structure with fibres which are adhesively bonded to one another in locations and that have a permeability for air of between 0.5 ml/min*cm² and 1.5 ml/min*cm².

Such fleece materials are used as medical fleece materials and can be flat, curved, flexible or, in particular, also cylinder-shaped. Depending on the embodiment, they are suitable for being placed permanently inside a human body as implants. This particularly applies to fleece materials made of polyurethane, which can be used, e.g. in a tube-like shape, as vascular prostheses. In this case, the fleece material can be used for forming a pipe wall, through which a canalization of blood becomes possible for the purpose of reconstructing degenerated blood vessels. It is referred in full here to EP 2 083 750 A1, as well as to WO 2011 054 932 A1, in which such fleece materials are described.

A material for the manufacture of vascular prostheses has to meet many requirements with regard to its properties, so that it can be used permanently for the formation of an artificial blood vessel. Aside from a sufficiently high mechanical and biological stability, it is particularly the biological compatibility of the material which constitutes a basic requirement when it comes to the suitability for being manufactured into an implantable medical product.

A vascular prosthesis should provide a reliable and permanent canalization of the blood stream, preventing any leakage or occlusion from occurring in the lumen of the prosthesis.

Aside from ruptures as the cause for leakages, it is substantially the material of the vascular prosthesis itself which can cause a leakage of blood. By way of example, the use of a woven textile as a material for a prosthesis wall may be mentioned here, which due to its porous structure cannot offer a reliable obturation against blood loss. Bleeding complications occur regularly after an implantation procedure, subsiding only after some time as the blood coagulation and the obturation of the pores that is caused by it set in. To accelerate this process, aids in the form of a sealing material are used for such materials to reduce severe bleeding complications. One such material is described in DE 600 03 046 T2.

Thanks to its design, the structure used in the present invention exhibits such a low level of porosity that bleeding caused by the prosthesis does not occur after the opening of a blood vessel. The permeability is chosen such that the blood cells penetrating the structure, and particularly the fleece material, immediately clog the pores of the material. In addition, a coagulation reaction occurs in the material, through which the vessel wall is additionally obturated.

In general, occlusions of the prosthesis lumen are biological reactions towards the foreign material. The occlusions are substantially caused by hyperplasia (excessive cell growth) occurring at the anastomoses or a thrombosis in the blood vessel.

Science has identified a compliance mismatch to be the main cause for the occurrence of hyperplasia at the anastomoses. This symptom occurs when the extensional properties of the prosthesis material significantly differ from those of the native vessel. The structure used in this invention comprises, particularly as the fleece material, a similar compliance as the human artery.

A thrombosis is formed in the lumen of a vascular prosthesis mainly as a result of an activation of thrombocytes at the site of the foreign material. Here, the material itself or its surface structure as well as the associated surface flow phenomena can be the cause of such an activation.

Thus, when it comes to providing an optimal material for a vascular prosthesis or a continuous obturation of a blood space, the goal is to make sure that the material is not identified by the blood cells as a disturbing foreign material. For this purpose, various technological approaches have been taken.

The medical fleece material of the company Nonwotecc which is described in EP 2 083 750 A1 as well as in WO 2011 054 932 A1, has structural characteristics of an extracellular matrix, so that endothelial cells can attach and spread on the inner surface of a prosthesis made from this material. The consequence of this cellular growth is the formation of a luminal endothelial cell layer which completely covers the underlying prosthesis material, thus considerably reducing coagulation activation in the blood.

The basic material used for manufacturing the fleece material has very good biocompatible properties, thanks to which only a minimal irritation of the thrombocytes is caused.

Finally, the elastic properties of the structure, and particularly of the fleece material, are dimensioned such that the vascular prosthesis made thereof has a compliance which is similar to the natural arterial vessel.

Based on this fact, the primary object of the invention is to prevent an undesired cell deposition at the structure and to increase the patency rate for the use as a vascular prosthesis.

This is achieved through an at least one-sided coating which reduces the permeability of the structure to less than 0.2 ml/min*cm².

Thus, a relatively impermeable membrane is coated, although a coating would no longer be necessary for the purpose of increasing the impermeability and a porous surface would be good for the cell growth.

For determining the permeability/porosity of the fleece material, a defined surface of the material is impinged with a defined air pressure, and afterwards the air volume stream that is flowing through the material is measured. This results in a special porosity, which can be indicated independently of the measuring method, for example as an air resistance value.

It would be advantageous if the fibres consisted of polyurethane.

Particularly when it comes to the manufacture of artificial vessels, the structure may comprise a fleece material, such as the one that is described in WO 2008/049386 A1, for example.

In an advantageous embodiment it is envisioned that the fibres are adhesively bonded to form a cylinder, and that the coating is disposed at the inside of the cylinder. Through the coating, sticking-out and possibly broken fibres which can lead to an activation of the thrombocytes in the passing stream of blood (thrombus formation) are smoothed out. Moreover, the entry of growth factors from the surrounding wound area is reduced, thus also diminishing the risk of hyperplasia in the anastomoses area.

The coating of the inner surface of the vascular prosthesis made from a medical fleece material surprisingly facilitates a further increase in the patency rate.

The results of the investigations carried out so far suggest that the likelihood of a long-term patency of the prosthesis is highest when the foreign body reaction is kept as weak as possible in the very beginning after the initial blood contact with the inner surface of the prosthesis. After this first time of contact, a lasting autologous coating of the material surface should occur through which the inner surface of the prosthesis is identified, as much as possible, to be tissue produced naturally in the body. In the optimal case, such an autologous coating consists of an unbroken layer of endothelial cells.

It is advantageous if the coating comprises gelatine, collagen and/or fibrin. Particularly gelatine can be resorbed after a selectively set period of time in order to make an apposition of endothelial cells on the underlying fiber structure possible.

A coat consisting of gelatine, fibrin and/or collagen renders the microscopically rough surface of the fleece material smoother, thus reducing the activation of thrombocytes that is caused by the flow. After a defined period of time which can be set by means of the manufacture of this coating, the coating is reabsorbed into the bloodstream, by and by uncovering the fleece material structure lying underneath, on which the endothelial cells may now attach.

What is more, through the coating described herein, the risk of hyperplasia is reduced due to the fact that an increased obturation of the inside of the vessel against the outside is effected, through which the inflow of growth factors from the wound area surrounding the vessel is prevented. These growth factors obviously have a promoting effect on the development of hyperplasia in the lumen of the prosthesis.

Additional suppression of hyperplasia can be achieved through the incorporation of medical drugs into the coating, which are then released in a time-controlled manner as the reabsorption of the coating is taking place. Thus, it is suggested that the coating should comprise a medical drug. For the prevention of inflammation, silver ions can be included into the coating.

The coating can be slowly absorbed when an implant such as, particularly, an implanted artificial vessel is used. It is advantageous if it is reabsorbed after the period of one to 30 days, and preferably after 2 to 14 days, up to maximally 10% of the original amount. A vivo model is suitable as a measuring method.

The invention claimed is:

1. An implant structure with fibers which are adhesively bonded to one another in locations, which have a permeability for air of between 0.5 ml/min*cm 2 and 1.5 ml/min*cm 2, wherein said structure with fibers has at least a one-sided coating, which reduces the permeability of the structure to less than 0.2 ml/min*cm 2.

2. The implant structure according to claim 1, wherein the fibers are made of polyurethane.

3. The implant structure according to claim 1, wherein the structure is a fleece material.

4. The implant structure according to claim 1, wherein the fibers are adhesively bonded to form a cylinder and the coating is disposed on the inside surface of the cylinder.

5. The implant structure according to claim 1, wherein the coating comprises gelatine.

6. The implant structure according to claim 1, wherein the coating comprises collagen.

7. The implant structure according to claim 1, wherein the coating comprises fibrin.

8. The implant structure according to claim 1, wherein the coating comprises a medical drug.

9. The implant structure according to claim 1, wherein the coating is reabsorbed after one to 30 days to no more than 10% of the original amount.

10. The implant structure according to claim 9, wherein the coating is reabsorbed after 2 to 14 days to no more than 10% of the original amount.

* * * * *